United States Patent [19]

Rajadhyaksha

[11] 4,424,210
[45] Jan. 3, 1984

[54] VEHICLE COMPOSITION CONTAINING 1-SUBSTITUTED AZACYCLOALKAN-2-ONES

[75] Inventor: Vithal J. Rajadhyaksha, Mission Viejo, Calif.

[73] Assignee: Nelson Research & Development Company, Irvine, Calif.

[21] Appl. No.: 328,445

[22] Filed: Dec. 7, 1981

Related U.S. Application Data

[60] Division of Ser. No. 137,248, Apr. 4, 1980, Pat. No. 4,316,893, which is a division of Ser. No. 725,490, Oct. 28, 1976, abandoned, which is a continuation-in-part of Ser. No. 588,247, Jun. 19, 1975, Pat. No. 3,989,816.

[51] Int. Cl.³ .............. A61K 31/30; A61K 31/70; A61K 31/71; A61K 31/505
[52] U.S. Cl. .......................... 424/180; 424/88; 424/181; 424/238; 424/240; 424/244; 424/251
[58] Field of Search .............. 424/244, 88, 251, 238, 424/240, 180, 181, 238

[56] References Cited

U.S. PATENT DOCUMENTS

| | | | |
|---|---|---|---|
| 3,332,938 | 7/1967 | Mayhew et al. | 260/293.3 |
| 3,551,554 | 12/1970 | Herschler | 424/274 |
| 3,891,757 | 5/1975 | Higuchi | 424/274 |
| 3,989,816 | 11/1976 | Rajadhyaksha | 424/181 |
| 3,991,203 | 11/1976 | Rajadhyaksha | 424/181 |
| 4,316,893 | 2/1982 | Rajadhyaksha | 424/180 |

*Primary Examiner*—Stanley J. Friedman
*Attorney, Agent, or Firm*—Martin A. Voet

[57] ABSTRACT

Compositions useful for carrying physiologically active agents such as therapeutic agents through skin and other body membranes comprising the agent and an effective, non-toxic amount of a compound having the structural formula

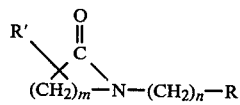

wherein R' is H or a lower alkyl group, m is 3–7, N is 0–17 and R is —CH₃, phenyl or substituted phenyl or

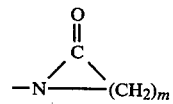

with the proviso that if m is 3 and R is —CH₃, then n is not 0–6.

16 Claims, No Drawings

VEHICLE COMPOSITION CONTAINING 1-SUBSTITUTED AZACYCLOALKAN-2-ONES

REFERENCE TO EARLIER FILED APPLICATION

This application is a division of application Ser. No. 137,248, filed Apr. 4, 1980, now U.S. Pat. No. 4,316,893, which in turn is a division of application Ser. No. 725,490 filed Oct. 28, 1976, now abandoned, which in turn is a Continuation-in-part of application Ser. No. 588,247, filed 6/19/75 now U.S., Pat. No. 3,989,816.

BACKGROUND OF THE INVENTION

Many physiologically active agents are best applied topically to obtain desirable results. Topical application, as contrasted to systemic application, largely avoids side effects of the agents and permits high local concentrations of the agents.

The greatest problem in applying physiologically active agents topically is that the skin is much an effective barrier to penetration. The epidermis of the skin has an exterior layer of dead cells called the stratum corneum which is tightly compacted and oily and which provides an effective barrier against gaseous, solid or liquid chemical agents, whether used alone or in water or oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use to treat such conditions as inflamation, acne, psoriasis, herpes simplex, eczema, infections due to fungus, virus or other microorganisms, or other disorders or conditions of the skin or mucous membranes, or of conditions beneath the exterior surface of the skin or mucous membranes. The stratum corneum also prevents the skin from absorbing and retaining cosmetic-type materials such as sunscreens, perfumes, mosquito repellants and the like.

Physiologically active agents may be applied to locally affected parts of the body through the vehicle system described herein. Vehicles such as USP cold cream, ethanol and various ointments, oils, solvents, and emulsions have been used heretofore to apply physiologically active ingredients locally. Most such vehicles are not effective to carry significant amounts of physiologically active agents through the skin. One such vehicle is dimethyl sulfoxide, which is described in U.S. Pat. No. 3,551,554. In this description, the term "animal" includes human beings as well as other forms of animal life, and especially domesticated animals and pets.

The l-lower alkyl substituted azacyclopentan-2-ones having 1-4 carbon atoms are known to moderately enhance percutaneous absorption of chemicals, e.g. drugs. It would be desirable to obtain the same or higher level of percutaneous absorption with substantially lower concentrations of the penetration-enhancing compound.

SUMMARY OF THE INVENTION

This invention relates to compositions for carrying physiologically active agents through body membranes such as skin and for retaining these agents in body tissues. More specifically, the invention relates to compositions useful in topically administerng a physiologically active agent to a human or animal comprising the agent and an effective, non-toxic amount of a compound having the structural formula

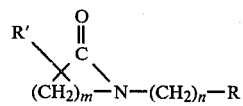

Where R' is H or a lower alkyl group having 1-4 carbon atoms, m is 3-7, n is 0-17, and R is —CH$_3$,

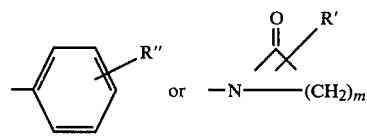

where R''=H or Halogen and R' has the same meaning as above, with the proviso that if m=3 and R= —CH$_3$ then n is not 0-6. In one preferred embodiment, R' is H, m is 3-7, R is —CH$_3$ or C$_6$H$_5$ and n is 0-11.

In another the preferred embodiment, R' is H, m, is 5-7 and R is CH$_3$ and n is 0-11. The preferred compound is 1-n-dodecylazacycloheptan-2-one.

It has been found that the physiologically active agents are carried through body membranes by the claimed vehicles and are retained in body tissue.

The invention further relates to vehicles themselves and their method of making.

DETAILED DESCRIPTION OF THE INVENTION

The claimed 1-substituted azacycloalkan-2-ones are made by methods described below and as further described in the Examples. Typical examples of compound included in the foregoing formula are the following:

1-n-hexylazacyclopentan-2-one
1-n-heptylazacyclopentan-2-one
1-n-octylazacyclopentan-2-one
1-n-nonylazacyclopentan-2-one
1-n-decylazacyclopentan-2-one
1-n-dodecylazacyclopentan-2-one
1-methylaacycloheptan-2-one
1-n-propylazacycloheptan-2-one
1-n-butylazacycloheptan-2-one
1-n-pentylazacycloheptan-2-one
1-n-hexylazacycloheptan-2-one
1-n-heptylazacycloheptan-2-one
1-n-octylazacycloheptan-2-one
1-n-nonylazacycloheptan-2-one
1-n-decylazacycloheptan-2-one
1-n-butylazacyclononan-2-one
1-n-octylazacyclononan-2-one
1-phenylazacyclopentan-2-one
1-benzylazacyclopentan-2-one
1-(2-chlorophenyl)azacyclopentan-2-one
1,3-Bis-(1-azacyclopentan-2-onyl)propane
1,6-Bis-(1-azacyclopentan-2-onyl)hexane The compounds covered by the general formula may be prepared by treating azacycloalkan-2-one with an alkyl or aralkyl halide or mesylate in the presence of a base, e.g. sodium hydride. The reaction is carried out under anhydrous conditions in a hydrocarbon solvent, for example, dry toluene at reflux temperature for about 10 to 72 hours in an inert atmosphere, for example, nitrogen. This method is outlined below:

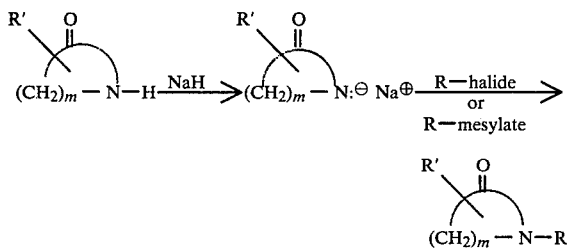

In the above method, substitution of an equimolar ratio of a dibromoalkane in place of an alkyl halide gives Bis-N-azacycloalkan-2-onyl alkane.

Alternatively, a lactone of an alkanoic acid may be heated with an alkyl, aryl or aralkyl amine (with or without solvent) for about 20 to 72 hours at about 180°–250° C. with removal of water to obtain the corresponding 1-substituted azacycloalkan-2-one as shown below:

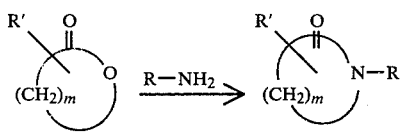

Similarly, heating a lactone of an alkanoic acid with a diaminoalkane in a 2.5 to 1 molar ratio gives the bis-N-aracycloalkan-2-onyl alkane.

In another method gamma-dialkylaminobutyric acid may be treated with phosphorous trihalide and the resulting acid halide (which need not be isolated) is heated, resulting specifically in the formation of N-alkylazacyclopentan-2-one. Suitable acid halide forming agents include phosphorous trichloride, phosphorous tribromide, thionyl chloride, etc. The acid halide is formed at room temperature and then the reaction temperature is raised to 70°–90° C. One of the alkyl groups on the amino nitrogen of the parent acid is eliminated as alkyl halide. If the alkyl groups on the amino nitrogen are different, the smaller of the two alkyl groups is eliminated preferentially. This method is described below.

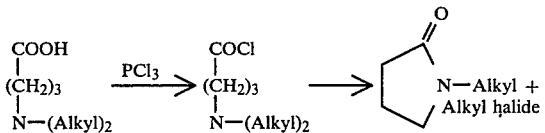

The amount of 1-substituted azacycloalkan-2-one which may be used in the present invention is an effective, non-toxic amount for enhancing percutaneous absorption. Generally, this amount ranges between about 0.01 to about 5 and preferably about 0.1 to 2 percent by weight of the composition.

The subject compositions may find use with many physiologically active agents which are soluble in the vehicles disclosed.

Fungistatic and fungicidal agents such as, for example, thiabendazole, chloroxine, amphotericin, candicidin, fungimycin, nystatin, chlordantoin, clotrimazole, ethonam nitrate, miconazole nitrate, pyrrolnitrin, salicylic acid, fezatione, ticlatone, tolnaftate, triacetin and zinc and sodium pyrithione may be dissolved in the vehicles described herein and topically applied to affected areas of the skin. For example, fungistatic or fungicidal agents so applied are carried through the stratum corneum, and thereby successfully treat fungus-caused skin problems. These agents, thus applied, not only penetrate more quickly than when applied in the vehicles of the prior art, but additionally enter the animal tissue in high concentrations and are retained for substantially longer time periods whereby a far more successful treatment is effected.

For example, the subject composition may also be employed in the treatment of fungus infections on the skin caused by candida and dermatophytes which cause athletes foot or ringworm, by dissolving thiabendazole or similar antifungal agents in one of the vehicles and applying it to the affected area.

The subject compositions are also useful in treating skin problems, such as for example, herpes simplex, which may be treated by a solution of iododeoxyuridine dissolved in one of the vehicles, or such problems as warts which may be treated with agents such as podophylline dissolved in one of the vehicles. Skin problems such as psoriasis may be treated by topical application of a solution of a conventional topical steroid in one of the vehicles or by treatment with theophylline or antagonists of β-adrenergic blockers such as isoproterenol in one of the vehicles. Scalp conditions such as alopecia areata may be treated more effectively by applying steroids such as triamcinolone acetonide dissolved in one of the vehicles of this invention directly to the scalp.

The subject compositions are also useful for treating mild eczema, for example, by applying a solution of fluocinolone acetonide or its derivatives; hydrocortisone, triamcinolone acetonide, indomethacin, or phenylbutazone dissolved in one of the vehicles to the affected area.

Examples of other physiologically active steroids which may be used with the vehicles include corticosteroids such as, for example, cortisone, cortodoxone, flucetonide, fludrocortisone, difluorsone diacetate, flurandrenolone acetonide, medrysone, amcinafel, amcinafide, betamethasone and its esters, chloroprednisone, clocortelone, descinolone, desonide, dexamethasone, dichlorisone, difluprednate, flucloronide, flumethasone, flunisolide, fluocinonide, flucortolone, fluoromethalone, fluperolone, fluprednisolone, meprednisone, methylmeprednisolone, paramethasone, prednisolone and prednisone.

The subject compositions are also useful in antibacterial chemotherapy, e.g. in the treatment of skin conditions involving pathogenic bacteria. Typical antibacterial agents which may be used in this invention include sulfonomides, penicillins, cephalosporins, penicillinase, erythromycins, lincomycins, vancomycins, tetracyclines, chloramphenicols, streptomycins, etc. Typical examples of the foregoing include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxytetracyclin minocycline, etc.

The subject compositions are also useful in protecting ultra-sensitive skin or even normally sensitive skin from damage or discomfort due to sunburn. Thus, dermatit's actinica may be avoided by application of a sunscreen, such as para-aminobenzoic acid or its well-known derivatives dissolved in one of the vehicles, to skin surfaces that are to be exposed to the sun; and the protective para-aminobenzoic acid or its derivatives will be carried into the stratum corneum more successfully and will therefore be retained even when exposed to water or washing for a substantially longer period of time than when applied to the skin in conventional vehicles. This invention is particularly useful for ordinary suntan lotions used in activities involving swimming because the ultraviolet screening ingredients in the carriers of the prior art are washed off the skin when it is immersed in water.

The subject compositions may also find use in treating scar tissue by applying agents which soften collagen, such as aminoproprionitrile or penecillamine dissolved in one of the vehicles of this invention topically to the scar tissue.

Agents normally applied as eye drops, ear drops, or nose drops are more effective when dissolved in the vehicles of this invention.

Agents used in diagnosis may be used more effectively when applied dissolved in one of the vehicles of this invention. Patch tests to diagnose allergies may be effected promptly without scratching the skin or covering the area subjected to an allergen when the allergens are applied in one of the vehicles of this invention.

The subject compositions are also useful for topical application of cosmetic or esthetic agents. For example, compounds such as melanin-stimulating hormone (MSH) or dihydroxy acetone and the like are more effectively applied to skin to simulate suntan when they are dissolved in one of the vehicles of this invention. The agent is carried into the skin more quickly and in greater quantity when applied in accordance with this invention. Hair dyes also penetrate more completely and effectively when dissolved in one of the vehicles of this invention.

The effectiveness of such topically applied materials as insect repellants or fragrances, such as perfumes and colognes, can be prolonged when such agents are applied dissolved in one of the vehicles of this invention.

It is to be emphasized that the foregoing are simply examples of physiologically active agents including therapeutic and cosmetic agents having known effects for known conditions, which may be used more effectively for their known properties in accordance with this invention.

In addition, the vehicles of the present invention may also be used to produce therapeutic effects which were not previously known. That is, by use of the vehicles described herein, therapeutic effects heretofore not known can be achieved.

As an example of the foregoing, griseofulvin is known as the treatment of choice for fungus infections of the skin and nails. Heretofore, the manner of delivery of griseofulvin has been oral. However, it has long been known that oral treatment is not preferred because of side effects resulting from saturation of the entire body with griseofulvin and the fact that only the outer layers of affected skin need to be treated. Therefore, because fungal infections are generally infections of the skin and nails, it would be advantageous to utilize griseofulvin topically. However, despite a long-felt need for a topical griseofulvin, griseofulvin has been used orally to treat topical fungus conditions because there was not heretofore known any formulation which could be delivered topically which would cause sufficient retention of griseofulvin in the skin to be useful therapeutically.

However, it has now been discovered that griseofulvin, in a range of therapeutic concentrations between about 0.1% and about 10% may be used effectively topically if combined with one of the vehicles described herein.

As a further example, acne is the name commonly applied to any inflammatory disease of the sebaceous glands; also *acne vulgaris*. The microorganism typically responsible for the acne infection is *Corynebacterium acnes*. Various therapeutic methods for treating acne have been attempted including topical antibacterials, e.g. hexachlorophene, and systemic antibiotics such as tetracycline. While the systemic antibiotic treatment are known to be partially effective, the topical treatments are generally not effective.

It has long been known that systemic treatment of acne is not preferred because of side effects resulting from saturation of the entire body with antibiotics and the fact that only the affected skin need by treated. However, despite a long-felt need for a topical treatment for acne, antibiotics generally have been used only systemically to treat acne because there was not heretofore known an antibacterial formulation which could be used topically which would be effective therapeutically in the treatment of acne. However, it has now been discovered that antibiotics, especially those of the lincomycin and erythryomycin families of antibiotics, may be used in the treatment of acne topically if combined with one of the vehicles described herein.

The antibiotics composition so applied is carried into and through the epidermis and deeper layers of the skin as well as into follicles and comedones (sebum-plugged follicles which contain *C. acnes*) in therapeutically effective amounts and thereby successfully may be used to temporarily eliminate the signs and symptoms of acne.

The term "physiologically active agent" is used herein to refer to a broad class of useful chemical and therapeutic agents including physiologically active steroids, antibiotics, anti-fungal agents, antibacterial agents, antineoplastic agents, allergens, antihistaminic agents, anti-inflammatory agents, ultraviolet screening agents, diagnostic agents, perfumes, insect repellants, hair dyes, etc.

Dosage forms for topical application may include solution nasal sprays, lotions, ointments, creams, gels, suppositories, sprays, aerosols and the like. Typical inert carriers which make up the foregoing dosage forms include water, acetone, isopropyl alcohol, freons, ethyl alcohol, polyvinyl pyrrolidone, propylene glycol, fragrances, gel-producing materials, mineral oil, stearyl alcohol, stearic acid, spermaceti, sorbitan monooleate, "Polysorbates", "Tweens", sorbital, methylcellulose, etc.

The amount of the composition, and thus of the physiologically active agent therein, to be administered will obviously be an effective amount for the desired result expected therefrom. This, of course, will be ascertained by the ordinary skill of the practioner. Due to enhanced activity which is achieved, the dosage of agent may often be decreased from that generally applicable. In accordance with the usual prudent formulating practices, a dosage near the lower end of the useful range of the particular agent may be employed initially and the dosage increased as indicated from the observed response, as in the routine procedure of the physician.

The examples which follow illustrate the vehicles and the compositions of the present invention. Temperatures are given in degrees Centigrade. All reactions involving sodium hydride were carried out in an inert nitrogen atmosphere.

EXAMPLE 1

Preparation of 1-n-Hexylazacyclopentan-2-one having the following structure

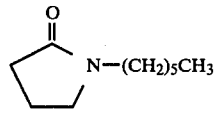

13.7 g of 50% sodium hydride-mineral oil dispersion (6.85 g NaH, 0.285 M) was placed in a 1 liter flask equipped with an addition funnel, condenser and a mechanical stirrer. This was washed with 2×100 ml of petroleum ether and the petroleum ether was decanted. About 250 ml of dry toluene was then added and to this stirred mixture was added dropwise a solution of 20.35 g (0.239 M) of azacyclopentan-2-one in 100 ml of dry toluene. Upon completion of addition the mixture was heated to reflux for 1 hour and then cooled to room temperature. A solution of 43.6 g (0.264 M) of 1-bromohexane in 100 ml of dry toluene was added dropwise for a period of one-half hour and thereafter the mixture was refluxed for 48 hours. After cooling to room temperature, the reaction mixture was filtered and the filter cake was washed with dry toluene. The combined filtrate was concentrated to a yellow oil. Distillation gave 25.7 g (63.5%) of colorless 1-n-Hexylazacyclopentan-2-one, boiling point 98°–102°/0.5 mm.

EXAMPLE 2

Preparation of 1-n-Heptylazacyclopentan-2-one having the formula:

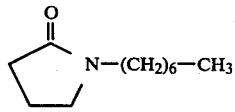

Following example 1, on refluxing 13 g of 50% oil dispersion of sodium hydride (6.5 g NaH, 0.271 M), 20.35 g (0.239 M) of azacyclopentan-2-one and 47.28 g (0.264M) of 1-bromoheptane in dry toluene for 21 hours was obtained 13.6 g (31%) of colorless oil; boiling point 115°–120°/0.6 mm.

EXAMPLE 3

Preparation of 1-n-Octylazacyclopentan-2-one

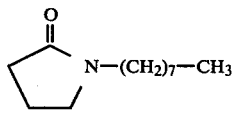

Following example 1, from 5.44 g of 57% of oil dispersion of sodium hydride (3.10 g NaH, 0.13 M), 10 g (0.1174 M) of azacyclopentan-2-one and 25.1 g (0.13 M) of 1-bromooctane was obtained 13.6 g (59%) of colorless 1-n-Nonylazacyclopentan-2-one. B.P. 123°–132°/0.3 mm.

EXAMPLE 4

Preparation of 1-n-Nonylazacyclopentan-2-one having the formula:

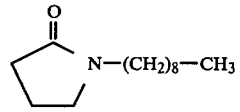

Following example 1, from 5.44 g of 57% sodium hydride-mineral oil dispersion (3.10 g NaH, 0.13 M), 10 g (0.1174 M) of a zacyclopentan-2-one and 27 g (0.13 M) of 1-bromononane was obtained 13.4 g (56%) of 1-n-Nonylazacyclopentan-2-one, b.p. 139°–143°/0.5 mm.

EXAMPLE 5

Preparation of 1-n-Decylazacyclopentan-2-one having the formula

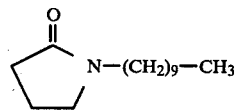

18.8 g (0.22 M) of γ-butyrolactone and 34.6 g (b 0.22 M) of n-decylamine were mixed and heated to 180° in a round bottom flask equipped with a condenser and a Dean-Stark trap for 22 hours. The dark brown reaction mixture was distilled at reduced pressure to yield 40.9 g (82.5%) of colorless product; b.p. 150°–155°/0.5-1 mm.

EXAMPLE 6

Preparation of n-Dodecylazacyclopentan-2-one having the formula

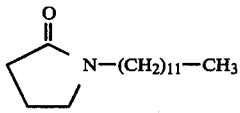

Following example 5, 18.8 g (0.22 M) of γ-butyrolactone and 37 g (0.2 M) of n-dodecylamine was heated for 24 hours. Distillation of the residue gave 40.7 g (80.3%) of 1-n-Dodecylazacyclopentan-2-one; b.p. 165°–170°/0.5 mm.

EXAMPLE 7

Preparation of 1-Methylazacycloheptan-2-one having the formula

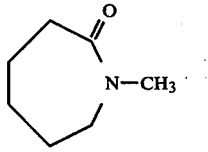

A suspension of 8.42 g of 57% sodium hydride-minera oil suspension (4.8 g NaH, 0.2 M) was washed with 2×400 ml portions of dry toluene and the toluene washings were decanted. 350 ml of dry toluene was added and the suspension was mechanically stirred while a solution of 20 g (0.177 M) of azacycloheptan-2-one in 50 ml of dry toluene was added dropwise over 1 hour. After the addition was over, the mixture was refluxed for 1 hour and then cooled to room temperature. 22.0 g (0.2 M) of methyl mesylate was added dropwise over 1 hour and the reaction mixture was then warmed to 50° for 1 hour. The mixture was cooled, filtered and the filter cake was resuspended in 100 ml of dry toluene and filtered. The combined filtrate was concentrated and the residue was distilled to yield 20 (88.85%) of 1-Methylazacycloheptan-2-one; b.p. 85°–87°/0.1 mm.

EXAMPLE 8

Preparation of 1-n-propylazacycloheptan-2-one having the formula

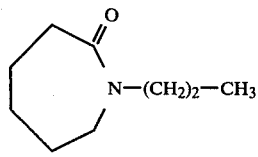

In a 1 liter 3-neck flask equipped with a dry ice-isopropanol condenser, an addition funnel and a mechanical stirrer was placed 10.2 g of 50% sodium hydride-mineral oil disperson (5.1 g NaH, 0.2125 M) and 150 ml of petroleum ether. The suspension was momentarily stirred and then sodium hydride was allowed to settle. Most of the petroleum either was pipetted out and 200 ml of dry toluene was added. To this was added dropwise a solution of 20 g (0.177 M) of azacycloheptan-2-one in 100 ml of dry toluene. The mixture was refluxed for 1 hour and then cooled to room temperature. A solution of 30.75 (0.25 M) of 1-bromopropane in 100 ml of dry toluene was added dropwise under stirring. Upon completion of the addition, the mixture was warmed to 80°–100° and the temperature was maintained there for 4 hours. Then the isopropanol-dry ice condenser was replaced with a water condenser and the reaction mixture was heated to reflux for 15 hours. The reaction mixture was cooled, filtered and the filtrate was concentrated to a yellow oil. Distillation afforded 22.2 g (81%) of colorless product; b.p. 83°–86°/0.25 mm.

EXAMPLE 9

Preparation of 1-n-Butylazacycloheptan-2-one having the formula

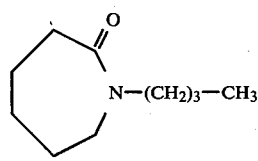

Following example 8, from 12.75 g of 50% sodium hydride-mineral oil dispersion (6.375 g NaH, 0.266 M), 25 g (0.221 M) of azacycloheptan-2-one and 34.25 g (0.25 M) of 1-bromobutane was obtained on 18 hr. reflux 26.8 g (72%) of colorless product; b.p. 95°–100°/0.3 mm.

EXAMPLE 10

Preparation of 1-n-Pentylazacycloheptan-2-one having the formula

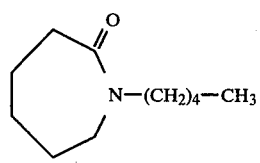

Following example 8 and using water condenser from the start of the reaction, 10 g of 50% sodium hydride-mineral oil dispersion (5 g NaH, 0.21 M), 20 g (0.177 M) of azacycloheptan-2-one and 30.2 g (0.2 M) of 1-bromopentane on 18 hr. reflux gave 23.3 g (87%) of colorless product; b.p. 110°–115°/0.3 mm.

EXAMPLE 11

Preparation of 1-n-Hexylazacycloheptan-2-one having the formula

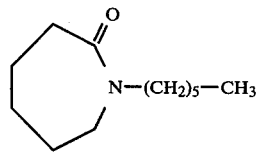

Following example 10, from 10.2 g of 50% sodium hydride-mineral oil dispersion (5.1 g NaH, 0.2125 M), 20 g (0.177 M) of azacycloheptan-2-one and 33 g (0.2 M) of 1-bromohexane on 19 hr. reflux was obtained 29.8 g (85.3%) of colorless product; b.p. 122°–128°/0.4 mm.

EXAMPLE 12

Preparation of 1-n-Heptylazacycloheptan-2-one having the formula

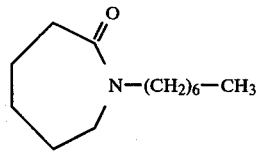

Following example 10, 10.2 g of 50% sodium hydride-mineral oil dispersion (5.1 g of NaH, 0.2125 M), 20 g (0.177 M) of azacycloheptan-2-one and 35.8 g (0.2 M) of 1-bromoheptane on 18 hr. reflux gave 33.5 g (90%) of colorless product; b.p. 155°–158°/0.5 mm.

EXAMPLE 13

Preparation of 1-n-Octalazacycloheptan-2-one having the formula

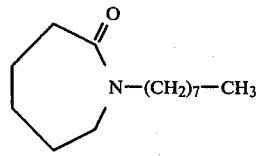

Following example 5, heating 17.5 g (0.153 M) of 6-hexanolactone and 22 g (0.17 M) of 1-aminooctane at 180° for 29 hr. gave 8.8 g (27%) of product; b.p. 155°-160°/0.5 mm.

EXAMPLE 14

Preparation of 1-n-Nonylazacycloheptan-2-one having the formula

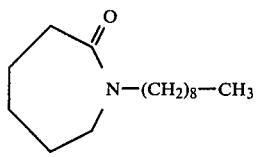

Following example 5, heating 22.83 g (0.2 M) of 6-hexanolactone and 28.65 g (0.2 M) of 1-aminononane at 180° for 20 hours gave 11.5 g (26%) of product; b.p. 155°-165°/0.6 mm.

(Higher yeilds of 1-n-Octyl- and 1-n-Nonylazacycloheptan-2-one may be obtained by use of the sodium hydride method).

EXAMPLE 15

Preparation of 1-n-Decylazacycloheptan-2-one having the formula

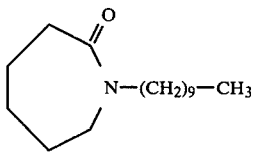

Following example 10, 10.2 g of 50% sodium hydride-mineral oil dispersion (5.1 g NaH, 0.2125 M), 20 g (0.177 M) of azacycloheptan-2-one and 44.2 g (0.2 M) of 1-bromodecane on 19 hr. reflux gave 38 g (84.7%) of product; b.p. 158°-163°/0.25-0.3 mm.

EXAMPLE 16

Preparation of 1-n-Dodecylazacycloheptan-2-One having the formula

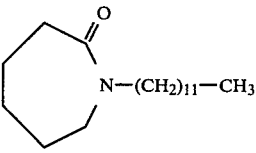

Following example 10, 15.3 g of 50% sodium hydride-mineral oil dispersion (7.65 g NaH, 0.319 M), 30 g (0.266 M) of azacycloheptan-2-one and 66.1 g (0.265 M) of 1-bromododecane on 20 hr. reflux gave 60 g (80%) of colorless product; b.p. 175°-180°/0.3 mm.

EXAMPLE 17

Preparation of 1-n-Butylazacyclononan-2-one having the formula

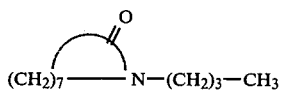

Following example 10, 16.32 g of 50% sodium hydride-mineral oil dispersion (8.16 g NaH, 0.34 M), 40 g (0.283 M) of azacyclononan-2-one and 43 g (0.311 M) of 1-bromobutane was refluxed for 22 hours. The reaction mixture was diluted with benzene-tolune and was extracted with water. The organic phase was separated, dried and concentrated to a yellow oil. Distillation afforded 41.4 g (74%) of product; b.p. 166°-170°/0.2 mm.

EXAMPLE 18

Preparation of 1-n-Octylazacyclononan-2-one having the formula

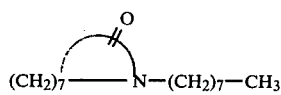

Following example 17, 4.2 g of 50% sodium hydride-mineral oil dispersion (2.1 g NaH, 0.0875M), 10 g (0.0708M) of azacyclononan-2-one and 15 g (0.0777M) -bromooctane gave 12.5 g (70%) of product; b.p. 150°-160°/0.5 mm.

EXAMPLE 19

Preparation of 1-Phenylazacyclopentan-2-one having the formula

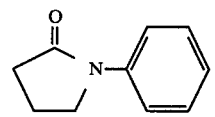

9.3 g (0.1M) of aniline and 9.5 g (0.11M) of γ-butyrolactone were mixed and heated to 200° for 48 hours. At the end of the reaction, unreacted starting materials and water were removed at reduced pressure. Distillation of the residue gave 6.3 g (39%) of the product (89% yield based on reclaimed aniline); b.p. 138°-140°/0.3 mm. Yield in this reaction can be improved if the water formed during the reaction is separated out with or without the use of a solvent (benzene or toluene).

EXAMPLE 20

Preparation of 1-Benzylazacyclopentan-2-one having the formula

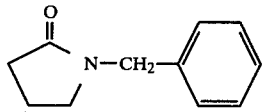

6.97 g (0.06M) of γ-butyrolactone is mixed with 6.97 g (0.065 M) of benzylamine and heated at 190° for 24 hours. Excess benzyl amine and water was distilled off and the residue was distilled to obtain 7.4 g (70%); b.p. 125°-130°/1 mm.

EXAMPLE 21

Preparation of 1-(2-chlorophenyl)azacyclopentan-2-one having the formula

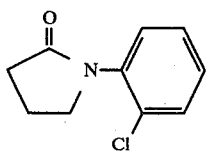

Following example 19, 12.57 g (0.1M) of 2-chloroaniline and 9.5 g (0.11M) of γ-butyrolactone were heated for 48 hours. The excess starging materials were removed at 50°–80°/0.3 mm. Distillation of the residue gave 4.9 g (25%) of product (45% based on recovered 2-chloroaniline); b.p. 150°–155°/0.3—0.4 mm.

EXAMPLE 22

Preparation of 1,3-Bis(1-azacyclopetan-2-onyl) propane having the formula

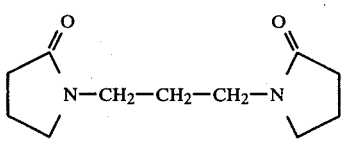

To 11.0 g of 57% sodium hydride-mineral oil suspension (6.27 g NaH, 0.261M) was added 150 ml of dry toluene and this was stirred for a few minutes. Toluene was decanted and 150 ml of fresh dry toluene was added. 20 g (0.235M) of azacyclopentan-2-one was added dropwise over 1 hour and after the addition was over the mixture was refluxed for 1 hour. 22.3 g (0.11M) of 1,3-dibromopropane was added dropwise over three hours. The refluxing was continued for 72 hours and then the reaction mixture was cooled and filtered twice, the second time through celite. The filtrate was concentrated and the residue was distilled to obtain 8.2 g (35.4%) of product; b.p. 179°–180°/0.03 mm.

EXAMPLE 23

Preparation of 1,6-Bis-(1-azacyclopentan-2-onyl) hexane having the formula

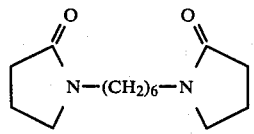

11.62 g (0.1M) of 1,6-diaminohexane and 21.66 g (0.25M) of γ-butyrolactone were mixed and heated to 150°–165° for 22 hours. Excess γ-butyrolactone was then distilled off at reduced pressure (80°/2mm). The light brown residue was poured into a crystallization dish where it immediately solidified. The solid was taken in chloroform, powdered, filtered and the tan powder was washed with chloroform. Yield 22.0 g (87%); melting point 101°–103°.

EXAMPLE 24

The following solution formulation is prepared:

|  | Solution (%) |
| --- | --- |
| Griseofulvin | 1 |
| 1-n-dodecylazacycloheptan-2-one | 1 |
| Isopropyl myristate | 5 |
| Fragrance | 0.1 |
| Ethanol | 92.9 |

This formulation is effective in the treatment of fungus infections.

EXAMPLE 25

An aerosol form of the formulation of Example 24 is prepared by preparing the following mixture:

| Formulation | 25% |
| --- | --- |
| Freon[1] | 75% |

[1]Freon is 75/25 Freon 114/12.

EXAMPLE 26

The following cream formulation is prepared:

|  | % |
| --- | --- |
| Clindamycin (base) | 1.0 |
| Stearyl alcohol, U.S.P. | 12.0 |
| Ethoxylated cholesterol | 0.4 |
| Synthetic spermaceti | 7.5 |
| Sorbitan monooleate | 1.0 |
| Polysorbate 80, U.S.P. | 3.0 |
| 1-n-dodecylazacycloheptan-2-one | 0.5 |
| Sorbitol solution, U.S.P. | 5.5 |
| Sodium citrate | 0.5 |
| Chemoderm #844 Fragrance | 0.2 |
| Purified water | 68.4 |

This formulation is effective in the treatment of acne.

EXAMPLE 27

The following solution formulations are prepared:

|  | A (%) | B (%) |
| --- | --- | --- |
| Clindamycin base | — | 1.0 |
| Clindamycin phosphate acid | 1.3 | — |
| Sodium hydroxide | 0.077 | — |
| 1.0 Molar hydrochloric acid | — | 2.27 |
| Disodium edetate.2H2O | 0.003 | 0.003 |
| Fragrances | 0.5 | 0.5 |
| 1-n-dodecylazacycloheptan-2-one | 1.0 | 1.0 |
| Purified water | 20.0 | 17.73 |
| Isopropanol | 77.12 | 77.497 |

These solutions are effective for the treatment of acne in humans.

EXAMPLE 28

The following solution formulation is prepared:

|  | % |
| --- | --- |
| Neomycin sulfate | 0.5 |
| Lidocaine | 0.5 |
| Hydrocortisone | 0.25 |
| 1-n-dodecylazacycloheptan-2-one | 0.5 |
| Propylene glycol | 98.25 |

This solution is effective for the treatment of otitis in domestic animals.

EXAMPLE 29

The following sunscreen emulsion is prepared:

|  | % |
| --- | --- |
| p-amino benzoic acid | 2.0 |
| Benzyl alcohol | 0.5 |
| 1-n-dodecylazacycloheptan-2-one | 1.0 |
| Polyethylene glycol 500-MS | 10.0 |
| Isopropyl lanolate | 3.0 |
| Lantrol | 1.0 |
| Acetylated lanolin | 0.5 |
| Isopropyl myristate | 5.0 |
| Light mineral oil | 8.0 |
| Cetyl alcohol | 1.0 |
| Veegum | 1.0 |
| Propylene glycol | 3.0 |
| Purified water | 64.0 |

EXAMPLE 30

The following antineoplastic solution is prepared:

|  | % |
| --- | --- |
| 5-Fluorouracil | 5 |
| 1-n-dodecylazacycloheptan-2-one | 0.1 |
| Polyethylene glycol | 5 |
| Purified water | 89.9 |

EXAMPLE 31

The following insect repellant atomizing spray is prepared:

|  | % |
| --- | --- |
| Diethyltoluamide | 0.1 |
| 1-n-dodecylazacycloheptan-2-one | 0.1 |
| Ethanol | 99.8 |

EXAMPLE 32

The following lotion formulation may be prepared containing about 0.001 to 1 percent, with preferably 0.1 percent fluocinilone acetonide:

|  | % |
| --- | --- |
| Fluocinolone acetonide | 0.001–1 |
| Cetyl alcohol | 15 |
| Propylene glycol | 10 |
| Sodium lauryl sulfate | 15 |
| 1-n-dodecylazacycloheptan-2-one | 1 |
| Water (to make 100%) |  |

The steroid is dissolved in the vehicle and added to a stirred, cooling melt of the other ingredients. The preparation is particularly useful for the treatment of inflammed dermatoses by topical application to the affected skin area. The amount and frequency of application is in accordance with standard practice for topical application of this steroid. Penetration of the steroid into the inflammed tissue is enhanced and a therapeutic level is achieved more rapidly and sustained for longer duration than when the steroid is applied in conventional formulations.

EXAMPLE 33

Examples 24–32 are repeated, except the 1-n-dodecylazacycloheptan-2-one is replaced with an equal amount of each of the following compounds:

1-n-hexylazacyclopentan-2-one
1-n-heptylazacyclopentan-2-one
1-n-octylazacyclopentan-2-one
1-n-nonylazacyclopentan-2-one
1-n-decylazacyclopentan-2-one
1-n-dodecylazacyclopentan-2-one
1-methylazacycloheptan-2-one
1-n-propylazacycloheptan-2-one
1-n-butylazacycloheptan-2-one
1-n-pentylazacycloheptan-2-one
1-n-hexylazacycloheptan-2-one
1-n-heptylazacycloheptan-2-one
1-n-octylazacycloheptan-2-one
1-n-nonylazacycloheptan-2-one
1-n-decylazacycloheptan-2-one
1-n-butylazacyclononan-2-one
1-n-octylazacyclononan-2-one
1-phenylazacyclopentan-2-one
1-benzylazacyclopentan-2-one
1-(2-chlorophenyl)azacyclopentan-2-one
1,3-Bis-(1-azacyclopentan-2-onyl)propane
1,6-Bis-(1-azacyclopentan-2-onyl)hexane Comparable results are obtained.

I claim:

1. A composition comprising an effective amount of a physiologiclly active agent and a non-toxic, effective penetrating amount of compound having the structural formula

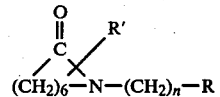

wherein R' is H or a lower alkyl group having 1–4 carbon atoms, n is 0–17 and R is —CH₃,

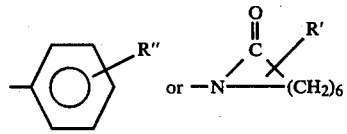

wherein R" is H or halogen.

2. The composition of claim 1 wherein the physiologically active agent is an antibacterial agent.

3. The composition of claim 2, wherein the antibacterial agent is an antibiotic.

4. The composition of claim 3 wherein the antibiotic is selected from the group consisting of lincomycin, clindamycin, erythromycin and pharmaceutically useful salts thereof.

5. The composition of claim 1 wherein the physiologically active agent is a physiologically active steroid.

6. The composition of claim 1 wherein the physiologically active agent is an antifungal agent.

7. The composition of claim 1 wherein the physiologically active agent is iododeoxyuridine.

8. The composition of claim 1 wherein the physiologically active agent is 5-fluorouracil.

9. A composition useful for topically administering a physiologically active agent to a human or animal comprising an effective amount of a physiologically active agent and a non-toxic, effective penetrating amount of a compound having the structural formula

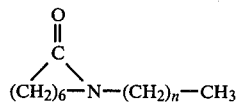

wherein n is 0–11.

10. The composition of claim 9 wherein the physiologically active agent is an antibacterial agent.

11. The composition of claim 9 wherein the antibacterial agent is an antibiotic.

12. The composition of claim 11 wherein the antibiotic is selected from the group consisting of lincomycin, clindamycin, erthromycin and pharmaceutically useful salts thereof.

13. The composition of claim 9 wherein the physiologically active agent is a physiologically active steroid.

14. The composition of claim 9 wherein the physiologically active agent is an antifungal agent.

15. The composition of claim 9 wherein the physiologically active agent is iododeoxyuridine.

16. The composition of claim 9 wherein the physiologically active agent is 5-fluorouracil.

* * * * *

UNITED STATES PATENT AND TRADEMARK OFFICE
CERTIFICATE OF CORRECTION

PATENT NO. : 4,424,210
DATED : January 3, 1984
INVENTOR(S) : Vithal J. RAJADHYAKSHA It is certified that error appears in the above-identified patent and that said Letters Patent are hereby corrected as shown below:

On the title page:
[54] In the title, "AZACYCLOALKAN" should read

-- AZACYCLOOCTAN --.

Signed and Sealed this

Third Day of April 1984

[SEAL]

Attest:

GERALD J. MOSSINGHOFF

Attesting Officer     Commissioner of Patents and Trademarks